(12) United States Patent
Mendel-Hartvig et al.

(10) Patent No.: US 6,812,038 B1
(45) Date of Patent: Nov. 2, 2004

(54) ASSAY DEVICE AND USE THEREOF

(75) Inventors: Ib Mendel-Hartvig, Uppsala (SE); Rune Björkman, Uppsala (SE)

(73) Assignee: Pharmacia Diagnostics AB, Uppsala (SE)

( * ) Notice: Subject to any disclaimer, the term of this patent is extended or adjusted under 35 U.S.C. 154(b) by 437 days.

(21) Appl. No.: 09/713,763

(22) Filed: Nov. 15, 2000

Related U.S. Application Data

(60) Provisional application No. 60/167,782, filed on Nov. 29, 1999.

(30) Foreign Application Priority Data

Nov. 18, 1999 (SE) ............................................ 9904175

(51) Int. Cl.$^7$ ............................................ G01N 33/558
(52) U.S. Cl. ........................... 436/514; 422/55; 422/56; 422/57; 422/58; 422/61; 435/7.9; 435/7.92; 435/287.1; 435/287.2; 435/287.7; 435/287.9; 435/288.4; 435/288.5; 435/288.7; 435/805; 435/810; 435/970; 435/975; 436/169; 436/172; 436/518; 436/525; 436/530; 436/805; 436/808; 436/810
(58) Field of Search .............................. 422/55–58, 61; 435/7.9, 7.92, 287.1, 287.2, 287.7, 287.9, 288.4, 288.5, 288.7, 805, 810, 970, 975; 436/169, 172, 514, 518, 525, 530, 805, 810, 808

(56) References Cited

U.S. PATENT DOCUMENTS 4,444,879 A * 4/1984 Foster et al. .................. 422/56
4,959,324 A    9/1990 Ramel et al.
5,260,221 A   11/1993 Ramel et al.

FOREIGN PATENT DOCUMENTS

| EP | 0320240 | 6/1989 |
|----|---------|--------|
| EP | 0427534 | 5/1991 |
| WO | WO 9119980 | 12/1991 |

* cited by examiner

*Primary Examiner*—Christopher L. Chin
(74) *Attorney, Agent, or Firm*—Dinsmore & Shohl LLP

(57) ABSTRACT

A test device and a kit for conducting an assay for the determination of an analyte in a sample comprises (i) a housing (1,2), and within said housing, (ii) a flow matrix (6) allowing liquid to be transported by capillary action and having at least one zone with immobilized capturing agent capable of directly or indirectly binding to the analyte, (iii) a liquid container (13) for sample liquid, and (iv) at least one liquid container for liquid other than sample liquid. The device further comprises (v) separation means (5) between the flow matrix (6) and the liquid containers (13), wherein said separation means (5) are mounted in movable relationship with the liquid containers to in a first position prevent liquid contact of the flow matrix (6) with the liquid containers (13), and in a second position permit liquid receiving contact of the flow matrix (6) with the liquid containers (13).

An assay method for determining an analyte in a sample wherein the sample and assay liquids are flown through a flow matrix to reach the reaction zone in a predetermined sequence uses the device for carrying out the method. The use of the device comprises testing for a allergy, inflammation or autoimmune disease.

27 Claims, 2 Drawing Sheets

ASSAY DEVICE AND USE THEREOF

RELATED APPLICATION

The present application claims priority under 35 U.S.C. §119 of U.S. application Ser. No. 60/167,782 filed Nov. 29, 1999.

FIELD OF THE INVENTION

The present invention relates to a novel solid phase assay device for conducting assays, especially immunochromatographic assays, for the determination of analytes in samples, and to methods of using the device.

Background of the Invention

A type of solid phase assay devices comprises a plate-shaped flow matrix of bibulous material, usually a membrane strip, such as of cellulose nitrate or glass fiber, in which liquid can be transported laterally (i.e. in the plane of the strip) by capillary forces in the membrane. The membrane usually has a sample application zone, and a a detection zone downstream of the sample application zone. In the detection zone, usually a capturing reagent for the analyte is immobilized. To conduct an assay, the application zone is contacted with the liquid sample to be assayed for the analyte of interest. The device is maintained under conditions sufficient to allow capillary action of liquid to transport the analyte of interest, if present in the sample, through the membrane strip to the detection zone where the analyte is captured. The capillary liquid flow is usually insured by an absorbing pad or the like at the downstream end of the strip. A detection reagent, usually labelled, is then added upstream of the detection zone and interacts with captured analyte in the detection zone, and the amount of captured analyte is measured. Often, the detection reagent is pre-deposited in or on the membrane strip, e.g. in the form of diffusively movable particles containing fluorophoric or chromogenic groups, either upstream of the sample application zone or between the sample application zone and the detection zone.

EP-A-306 336 discloses an assay device of the general type outlined above, wherein the strip of bibulous material is enclosed in a housing. The housing has a first opening for introducing the sample into the device, and second opening for introducing another liquid reagent than the sample into the device, such as a member of the signal producing system used. The device can also include additional means than the two openings for introducing additional assay reagents into the device, e.g. a third opening in the housing or a breakable container with liquid reagent included in the device. The device is said to permit timed reagent additions even though the operator carries out all the steps in rapid succession.

WO 99/36776 discloses an assay method of the general type described above based on the discovery that zonewise migration of desired assay liquids in a predetermined order may be obtained if the liquids are added simultaneously or almost simultaneously to adjacent zones in the strip.

Carrying out an assay with one of the devices described in the two publications mentioned above require, however, a number of steps to be taken by the operator in a short time, and especially the simultaneous addition of liquids according to the method of WO 99/36776 may be difficult or inconvenient for the operator to perform.

SUMMARY OF THE INVENTION

An object of the present invention is to provide an assay device for conducting an assay for the determination of an analyte, which device permits simultaneous initiation of flow of sample and at least one other assay liquid.

Another object of the present invention is to provide an assay device which is suitable for performing a sequential assay with a predetermined flow of sample and assay liquids through the device.

Still another object of the present invention is to provide a device which is easy to handle for the operator and requires a minimum of operation steps.

According to the present invention, the above and other objects and advantages are obtained with a test device for conducting an assay for the determination of an analyte in a sample, which device comprises (i) a housing, and within said housing, (ii) a flow matrix allowing liquid to be transported by capillary action and having at least one zone with immobilized capturing agent capable of directly or indirectly binding the analyte, (iii) a liquid container for sample liquid, and (iv) at least one liquid container for liquid other than sample liquid. The device is characterized in that it further comprises (v) separation means between the flow matrix and the liquid containers, wherein said separation means are mounted in a movable relationship with the liquid containers to in a first position prevent liquid contact of the flow matrix with the liquid containers, and in a second position permit liquid receiving contact of the flow matrix with the liquid containers.

The flow matrix is preferably plate or sheet shaped, such as a membrane strip, which allows lateral liquid flow therethrough.

The term "liquid container" is to be interpreted broadly and basically encompasses any liquid holding element or means capable of receiving and delivering liquid. Thus, the liquid contaner may be a receptacle or well with the opening facing the flow matrix, wherein the opening is closed or sealed by the above-mentioned liquid-tight element. The liquid container may also be a body capable absorbing and holding a predetermined amount of aqueous liquid, such as, for example, a pad or a sponge body. Usually, such a body is enclosed in a well or other room sealed by the liquid-tight element.

In one embodiment, the liquid containers are mounted adjacent to a face, usualy the top face, of the flow matrix, and the separation means comprise a flat liquid-tight element sandwiched between the liquid containers and the flow matrix. Preferably, this liquid-tight element is at least partially removable from the housing and may, for example, be a pull-out film.

In an alternative embodimnent, the liquid containers are mounted in a movable relationship with the flow matrix, i.e. in a position, the liquid containers are separated from the flow matrix, and may be brought to a second position where the containers are in liquid transferring contact with the flow matrix.

DETAILED DESCRIPTION OF THE INVENTION

Figure 1:
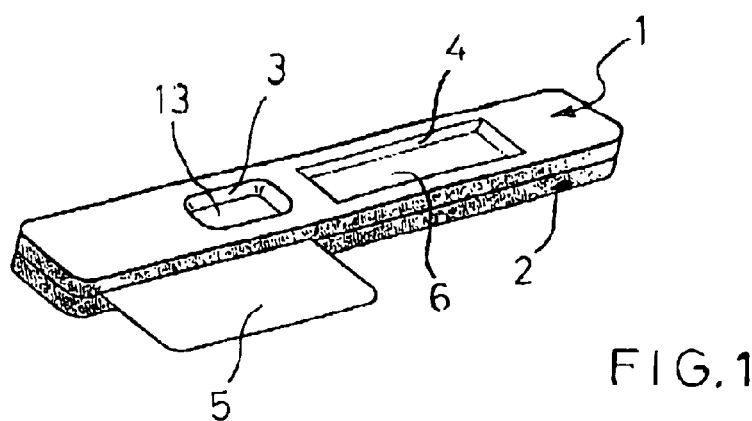
FIG. 1 is a perspective view of an embodiment of a device according to the present invention.

As best shown in FIG. 1, the device illustrated in FIGS. 1 to 5 comprises an upper housing part 1 and lower housing part 2 of a material which is insert with respect to the sample and any reagents used in the assays to be conducted with the device, e.g. polystyrene or polypropylene. The upper housing part 1 leas a sample well aperture 3 (here conical) and a detection window 4. Also shown in FIG. 1 is a removable separation means 5 to be described below.

Figure 2:
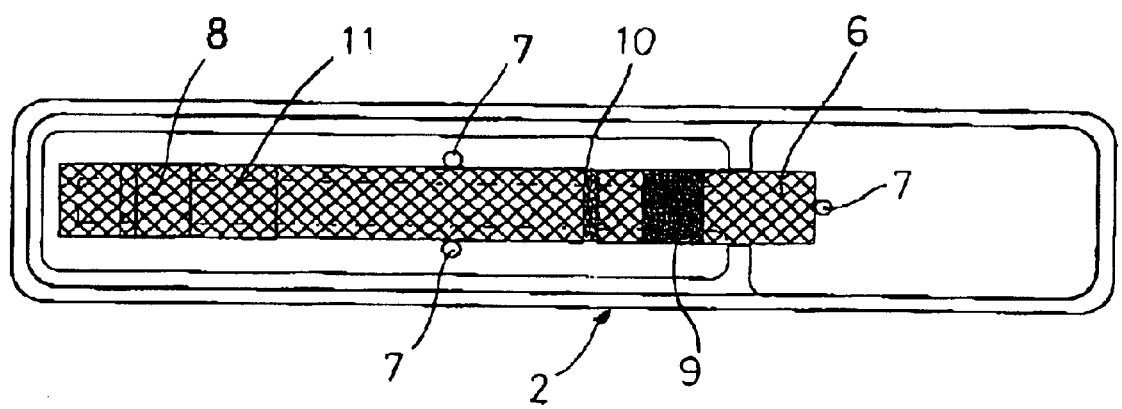
FIG. 2 is a top view of the lower part of the device in FIG. 1.
Figure 3:
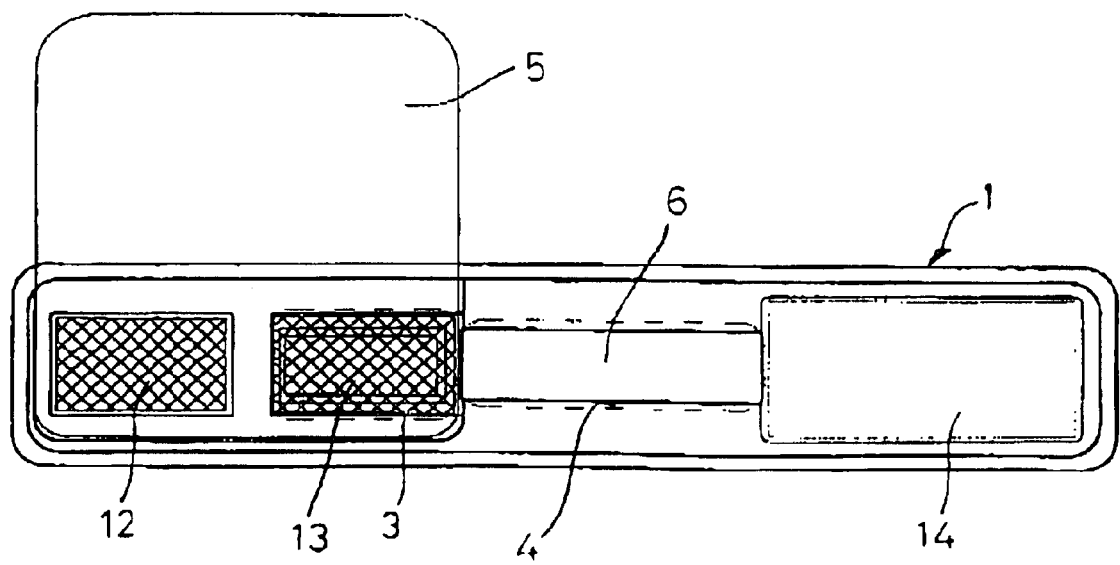
FIG. 3 is a partially transparent bottom view of the upper part of the device in FIG. 1.
Figure 4:
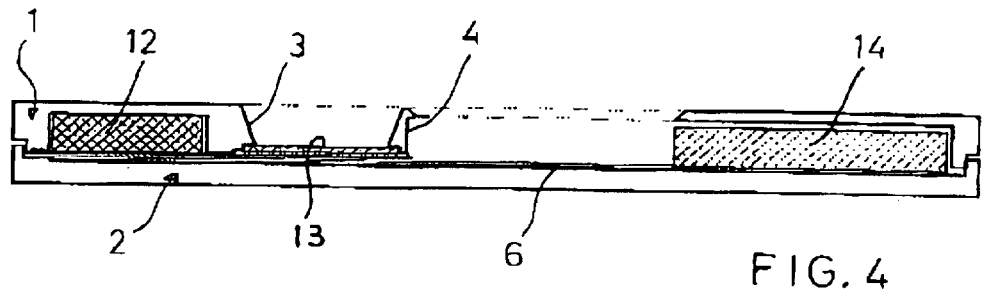
FIG. 4 is a sectional side view of the device in FIG. 1.
Figure 5:
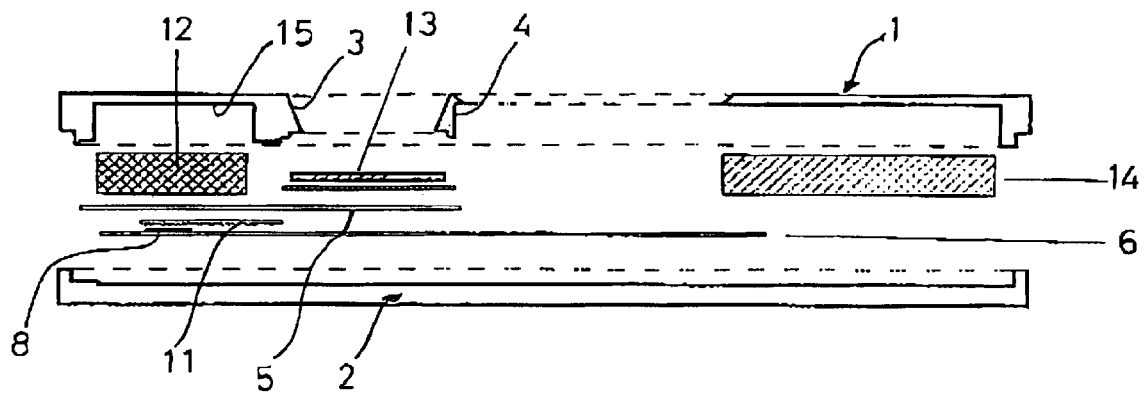
FIG. 5 is an exploded view corresponding to the side view in FIG. 4.

With reference now to primarily to FIG. 2, but also to FIGS. 3 to 5, the lower housing part 2 has mounted therein a test strip 6 of bibulous material (i.e. a porous material susceptible to traversal of an aqueous medium due to capillary action), e.g. nitrocellulose on a polyester backing. In order to avoid capillary effects along the edges of the strip, the strip 6 is mounted on a ridge (dashed line) in the housing part bottom, the ridge being narrower than the width of the strip. The positioning of the strip 6 in the housing is facilitated by guide means 7. Near the upstream end of the strip 6 (to the left in FIG. 2), a filter piece 8, containing a diffusively movable detection reagent, is placed on the strip. Such a detection reagent may, for example, be a conjugate between a label particle and a reactant capable of binding to the analyte. Further downstream, and placed below and within the detection window 4, there is a reaction zone 9 on the strip which contains an immobilized reactant capable of binding an analyte to be tested for. In the illustrated case, there is also a calibrator zone 10 containing a predetermined amount of immobilized calibrator substance, for example analyte. Also depicted on the membrane strip 6 is a flow barrier 11 here specifically a piece of a film element, which covers the filter piece 8 and extends towards the opening 3 in the housing part 1. The function of the flow barrier 11 will be described further on.

Turning specifically to FIGS. 3 to 5, the upper housing part 1 contains at the upstream end of the membrane strip 6, a pad 12 of liquid absorbing material intended to serve as a container for flow liquid, or buffer. The opening 3 in housing part 1 (FIG. 1) is intended for introducing sample to the membrane 6. In the illustrated case, a filter element 13 (which optionally may consist of two or more separate filters), is provided below the opening 3 for assays where the sample liquid needs to be filtered, e.g. when the sample is whole blood and blood cells are to be separated off. The buffer pad 12 thus forms a buffer liquid container, below referred to as buffer pad, and the room defined by the sample opening 3 and the filter element 13 forms a sample well, or sample container.

At the downstream end of the membrane strip 6, a pad 14 of absorbent material is placed, the purpose of which is to assist in maintaining a capillary flow of assay liquids through the membrane strip 6.

The above-mentioned separation element 5, here a liquid-tight pull-out film, is mounted at the upstream part of the membrane strip 6 to prevent contact between the membrane strip 6 and the bottom parts of the buffer pad 12 and sample filter 13, respectively. The film 5 is arranged to be manually removed by pulling it away from the device to thereby expose the top face of the membrane strip 6 to the buffer pad 12 (except the part of the membrane strip covered by the flow barrier film 11) and the sample filter 13, respectively, such that the membrane strip 6 is brought into simultaneous or close to simultaneous liquid receiving contact with the buffer pad 12 and the filter 13 in the sample well 3. The upper housing part 1 has a recess 15 for the buffer pad 12 designed to press the pad against the pull-out film 5, and thereby against the membrane strip 6 and flow film 11 when the pull-out film 5 is removed. To insure a liquid-tight enclosure of the pad 12 in the recess 5, the pull out film is tightly sealed against the edges of the recess 15, e.g. by welding. While in the illustrated case above, the pull-out film 5 is intended to be removed completely from the device, it is of course, sufficient that the film 5 is withdrawn from the membrane strip 6 to such an extent that the membrane strip surface parts in question are exposed to the sample and buffer liquids, respectively.

An assay for an analyte in a sample may be performed with the device described above as follows.

The device is usually provided ready for use with the buffer pad 12 soaked with buffer solution (flow liquid), with the detection reagent pre-deposited in the filter 8, and with the respective appropriate capture reagents immobilized in the reaction (or detection) zone 9 and the calibration zone 10, respectively. If the analyte to be tested for is, say, an antigen, the detection reagent in the filter 8 may, for example, be an antibody to the antigen coupled to a fluorogen-labelled particle, the immobilized reactant in the reaction zone 9 may be an antibody to the antigen, and the calibrator in the calibration zone 10 may be the analyte or an analyte analogue.

A predetemined amount of sample is added through the opening 3 in the housing part 1. All the necessary assay liquids, i.e. in this case sample liquid and buffer liquid, are then present in the device, the pull-out film 5, however, effectively preventing contact between the respective liquids and the membrane strip 6. The assay is then started by the operator removing the pull-out film 5 to thereby put the membrane strip 6 in simultaneous liquid receiving contact with the buffer pad 12 and the sample liquid in the sample well 3.

Buffer liquid from the pad 12 will now penetrate into the membrane strip 6 via the far upstream end part thereof which is in direct contact with the pad 12 (see FIG. 5) and be transported downstream the membrane strip 6 by capillary force. Simultaneously, sample liquid will penetrate into the membrane strip 6 and be transported in the downstream direction of the strip. There will thus be a flow of sample liquid directly followed by a flow pulse of buffer liquid. However, the detection reagent filter 8 and a major part of the buffer pad 12 are separated from the membrane strip 6 by the flow barrier film 11. Buffer liquid that has been transported into the membrane strip 6 will penetrate into and be transported through the filter 8 and bring the detection reagent deposited therein with it forming a detection reagent pulse. This detection reagent flow pulse will follow in sequence after the sample flow and the buffer flow pulse. Buffer that is transported in the membrane strip 6 after the detection reagent has been removed from the filter 8 will form a second buffer flow pulse following after the detection reagent flow pulse.

The above-mentioned different liquid flows will be transported along the membrane strip 6 in the indicated sequence, i.e. sample flow, first buffer flow, detection reagent flow, and second buffer flow, and will eventually reach the calibrator zone 10 and the reaction zone 9. In the reaction zone 9, analyte present in the sample will be captured by the reagent immobilized in the membrane. The analyte/capture reagent complex formed will be washed by the following first buffer flow, and the analyte-reagent complex will then react with detection reagent contained in the detection reagent flow to form a detectable detection reagent/capture reagent complex. The latter will finally be washed by the second buffer flow. In the calibration zone 10, the predetermined amount of analyte therein will react with the detection reagent in the detection reagent flow to form a detectable detection reagent/analyte complex. The flow liquid from the buffer pad 12 will thus in sequence wash, dissolve detection reagent, and wash. By measuring, through the detection window formed by the opening 4 in the housing part 1, the signal intensity from the detection reagent captured in the reaction zone 9 and correlating it with that obtained in the calibration zone 10, the amount of analyte in the sample may be determined.

Figure 6:
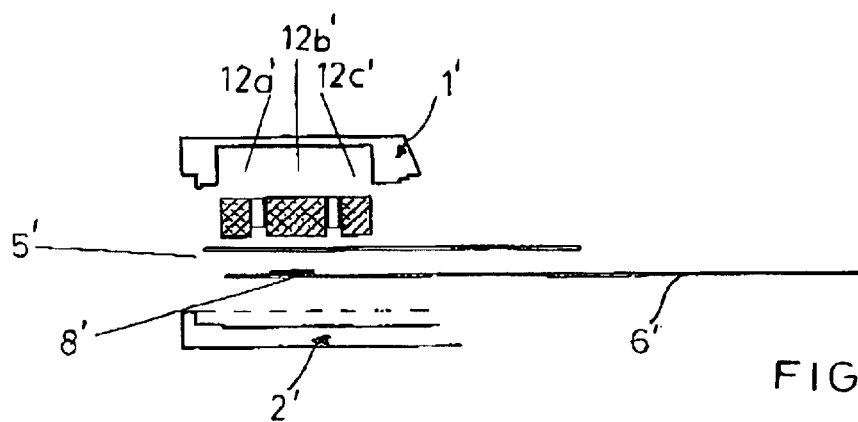
FIG. 6 is an exploded paal view of another embodiment of device according to the present invention.

As apparent from the above, an assay with the described device is easy and convenient to perform and provides for simultaneous initiation of the different assay liquid flows. Thus, once the sample has been added to the sample well, the pull-out film may be removed. The liquid in the buffer pad and the sample will thereby be brought into contact with the membrane strip and the desired sequential transport of the different liquid flows will start FIG. 6 illustrates a variant embodiment of device according to the present invention. This embodiment differs from that in FIGS. 2 to 5 in that (i) the single buffer pad 12 in the embodiment of FIGS. 2 to 5 has been replaced by three different buffer pads 12'*a*, 12'*b* and 12'*c*, (ii) the flow barrier film 11 is omitted and the detection reagent filter, here designated 8', is placed below the central buffer pad 12'*b*. Also this embodiment will give the same sequence of liquid flows as that in FIGS. 2 to 5 once the pull-out film 5 has been removed, i.e. sample flow, first wash flow, detection reagent flow, and second wash flow.

In another variation of device according to the present invention, the buffer pads 12'*a* and 12'*b* in FIG. 6 are combined to a single buffer pad, and the detection reagent filter 8' in FIG. 6 (with or without flow barrier film similar to the barrier film 11 in FIG. 5) is placed below the downstream part of the combined buffer pad. Also this embodiment will provide the same sequence of liquid flows upon removal of the pull-out film. The buffer 12'*c* will wash, and the combined buffer pad 12'*a*, 12'*b* will dissolve detection reagent and then wash.

Still another variation of device according to present invention has the buffer pad arrangement of FIG. 6 with three separate bulfer pads 12'*a*, 12'*b* and 12'*c* but the detection reagent filter 8 in FIGS. 2–5 is removed and the detection reagent is pre-deposited dissolved in the central buffer pad 12'*b*. Optionally, one or both of the two flanking buffer pads 12'*a* and 12'*c* may be omitted in this embodiment.

Other buffer pad arrangements as well as other variations and changes of the device which has been described above by way of example only, will be obvious to the skilled person.

In the reaction (or detection) zone described above, a reactant capable of specifically binding the analyte is immobilized (by covalent binding, via physical adsorption, via biospecific affinity, via immobilized particles to which the reactant is covalently bound, etc.). However, instead an agent capable of reacting with the reactant may be immobilized in the membrane, and the reactant may then be added together with the sample, or be pre-deposited in the membrane in an area or zone upstream of the reaction zone. Such an agent may be one member of a specific binding pair (sbp) and the reactant is then coupled or conjugated to the other member of the spb. Exemplary specific binding pairs include immunological binding pairs, such as antigen-antibody and hapten-antibody, biotin-avidin or streptavidin, lectin-sugar, hormone-hormone receptor, nucleic acid duplex. For example, the reaction zone may have streptavidin immobilized therein and the capture reactant for tle analyte may be biotinylated.

Similarly, the calibration zone may contain a binder for the calibrator substance rather than the calibrator substance per se. The binder is usually a member of a specific binding pair, such as one of those mentioned above, whereas the other member of the specific binding pair is coupled or conjugated to the calibrator substance, which may in turn be added with the sample or pre-deposited upstream of the calibrator zone. Streptavidin, for example, may be immobilized in the calibrator zone while the calibrator substance is biotinylated.

For further details on assay devices of the type contemplated herein, and particularly regarding flow matrixes, sequential assays, calibrator systems and detection reagents, it may be referred to our published international applications WO 99/36776, WO 99/36777 and WO 99/36780, for example.

Analytes to be determined using the present device are readily apparent to the skilled person. Usually, however, the analyte is a biospecific affinity reactant, e.g. an antibody or other protein, hapten, nucleic acid or polynucleotide, such as a DNA sequence. In the latter case the reaction zone may contain streptavidin and the DNA sequence to which the analyte sequence is to hybndize may be biotinylated.

The present device permits convenient pretreatment of the sample before starting that assay.

The present device may also be adapted for performing assays of the type described in our PCT application PCT/SE99/00722 where the flow matrix contains a chromatographic separation zone upsteam of the reaction (detection) zone to separate sample components which would otherwise disturb or influence the determination of the analyte.

While the invention has been described and pointed out with reference to operative embodiments thereof, it will be understood by those skilled in the art that various changes, modifications, substitutions and omissions can be made without departing from the spirit of the invention. It is intended therefore that the invention embraces those equivalents within the scope of the claims which follow.

What is claimed is:

1. A test device for conducting an assay for the determination of an analyte in a sample, the test device comprising (i) a housing, and within said housing, (ii) a flow matrix allowing liquid to be transported by capillary action and having at least one zone with immobilized capturing agent capable of directly or indirectly binding to the analyte, (iii) a liquid container for sample liquid, (iv) at least one liquid container for liquid other than sample liquid in the form of an absorbent pad or sponge, and (v) separation means between the flow matrix and the liquid containers, wherein said separation means are mounted in a movable relationship with the liquid containers between a first position wherein the separation means prevent liquid contact of the flow matrix with the liquid containers, and a second position wherein the separation means permit liquid receiving contact of the flow matrix with the liquid containers.

2. The test device according to claim 1, wherein the flow matrix is flat and the liquid flow is lateral within said matrix.

3. The test device according to claim 1 wherein the flow matrix is a membrane strip.

4. The test device according to claim 2 wherein the liquid containers are mounted adjacent to a face of said flow matrix, and the separation means comprise a flat liquid-tight element sandwiched between the liquid containers and the flow matrix.

5. The test device according to claim 4, wherein the liquid-tight element is at least partially removable from the housing.

6. The test device according to claim 5, wherein the liquid-tight element is a pull-out element.

7. The test device according to claim 1, wherein the liquid containers are mounted in a movable relationship with the flow matrix.

8. The test device according to claim 1, wherein the at least one liquid container for liquid other than sample liquid comprises at least one container with flow liquid.

9. The test device according to claim 1, wherein the at least one liquid container for liquid other than sample liquid comprises a container for an analytically detectable reagent.

10. The device according to claim 9, wherein at least one liquid container for flow liquid is provided upstream and/or downstream of said container with analytically detectable reagent.

11. The test device according to claim 1, wherein the flow matrix comprises a zone having an analytically detectable reagent predeposited in the matrix or in an element placed on the matrix.

12. The test device according to claim 11, wherein the at least one container for liquid other than sample liquid comprises a first container for flow liquid provided above and along said zone with analytically detectable reagent.

13. The test device according to claim 12, wherein at least one second container for flow liquid is provided upstream of said first container, and/or at least one third container is provided downstream of said first container.

14. The test device according to claim 11, wherein the at least one container for liquid other than sample liquid comprises a first container for flow liquid extending both upstream of and at least partially above and along said zone with analytically detectable reagent.

15. The test device according to claim 12, wherein at least one second container for flow liquid is provided downstream of said first container.

16. The test device according to claim 14 wherein a barrier element extends above said zone with analytically detectable reagent to prevent direct contact between said first container for flow liquid and the zone with analytically detectable reagent, when said separation means is in said second position.

17. The test device according to claim 1, wherein the capturing agent immobilized in the flow matrix is a member of a specific binding pair and wherein the other member of the specific binding pair is part of or coupled to a reagent capable of binding the analyte.

18. The test device according to claim 17, wherein the said specific binding pair is antigen-antibody, hapten-antibody, biotin-avidin, biotin-streptavidin or a nucleic acid duplex.

19. The test device according to claim 9, wherein the analytically detectable reagent is labelled.

20. The test device of claim 5, wherein the liquid-tight element comprises a pull-out sheet or a film.

21. The test device of claim 8, wherein the flow liquid comprises a buffer solution.

22. The test device of claim 19, wherein the analytically detectable reagent is labelled by a fluorophore or a chromophore.

23. The test device of claim 1, wherein the flow matrix is continuous.

24. A method of performing an assay for determining an analyte in a sample, which method comprises flowing sample and assay liquids through a test device according to claim 1, wherein the sample and assay liquids flow through the flow matrix to reach the zone in said flow matrix in a predetermined sequence, and detecting analyte bound in the zone.

25. The method according to claim 24 for testing for an analyte indicating a disease selected from allergy, inflammation and autoimmune diseases.

26. The method according to claim 25 wherein the analyte is a specific immunoglobulin.

27. A kit for conducting an assay method, which kit comprises a plurality of the test devices.

* * * * *

UNITED STATES PATENT AND TRADEMARK OFFICE
CERTIFICATE OF CORRECTION

PATENT NO. : 6,812,038 B1
DATED : November 2, 2004
INVENTOR(S) : Ib Mendel-Hartvig et al.

It is certified that error appears in the above-identified patent and that said Letters Patent is hereby corrected as shown below:

Column 8,
Line 40, after "test devices", insert -- of claim 1 --.

Signed and Sealed this

Twenty-sixth Day of April, 2005

JON W. DUDAS
*Director of the United States Patent and Trademark Office*